(12) United States Patent  
Schoenberg

(10) Patent No.: US 11,929,155 B1  
(45) Date of Patent: Mar. 12, 2024

(54) APPARATUS, SYSTEM AND METHOD FOR PREDICTIVE PROCESSING OF ELECTRONIC HEALTH DATA FOR NOTIFICATION SYSTEM

(71) Applicant: ALLSCRIPTS SOFTWARE, LLC, Chicago, IL (US)

(72) Inventor: Steve Schoenberg, Chicago, IL (US)

(73) Assignee: Allscripts Software, LLC, Chicago, IL (US)

( * ) Notice: Subject to any disclaimer, the term of this patent is extended or adjusted under 35 U.S.C. 154(b) by 124 days.

(21) Appl. No.: 16/183,685

(22) Filed: Nov. 7, 2018

Related U.S. Application Data

(63) Continuation-in-part of application No. 15/994,880, filed on May 31, 2018.

(51) Int. Cl.
| | | |
|---|---|---|
| *G16H 10/60* | (2018.01) | |
| *G06F 17/18* | (2006.01) | |
| *G06N 3/08* | (2023.01) | |
| *G16H 50/20* | (2018.01) | |
| *G16H 80/00* | (2018.01) | |

(52) U.S. Cl.  
CPC ............. *G16H 10/60* (2018.01); *G06F 17/18* (2013.01); *G06N 3/08* (2013.01); *G16H 50/20* (2018.01); *G16H 80/00* (2018.01)

(58) Field of Classification Search  
CPC ........ G16H 10/60; G16H 20/00; G16H 20/10; G16H 80/00; G16H 50/20; H04L 2209/24; H04L 63/062; H04L 63/102; H04L 63/104; H04L 63/105; H04L 9/0643; H04L 9/0861; H04L 2209/88; H04L 9/0836; H04L 9/088; G06F 17/18; G06N 3/08  
See application file for complete search history.

(56) References Cited

U.S. PATENT DOCUMENTS

| | | | | |
|---|---|---|---|---|
| 10,522,134 | B1 * | 12/2019 | Matsoukas | .............. G10L 15/01 |
| 2001/0039504 | A1 * | 11/2001 | Linberg | .............. G06F 19/3418 |
| | | | | 705/3 |
| 2011/0099024 | A1 * | 4/2011 | Lee | ......................... G16H 50/20 |
| | | | | 705/2 |

(Continued)

FOREIGN PATENT DOCUMENTS

| | | | | |
|---|---|---|---|---|
| WO | WO-2017023386 | A9 * | 3/2017 | ............. H04L 67/10 |
| WO | WO-2018152410 | A1 * | 8/2018 | ......... G06F 21/6245 |

*Primary Examiner* — Eliza A Lam  
(74) *Attorney, Agent, or Firm* — Peter Zura; LOZA & LOZA, LLP

(57) ABSTRACT

A system, apparatus and method for configuring notifications pursuant to a medical regimen for a patient. A communications interface receives patient data and patient feedback data associated with the patient and system patient data associated with other patients may be stored. A data model is processed for the medical regimen to calculate a baseline notification schedule based on the patient data, wherein the baseline notification schedule includes content and notification frequency for individual notifications. The patient data is processed to determine word vectors and embedded vectors. Statistical/predictive processing is executed on the processed patient feedback data to determine a patient characteristic. As a result of the statistical/predictive processing, the baseline notification schedule is modified to form a modified schedule for transmission in the system.

20 Claims, 12 Drawing Sheets

(56) References Cited

U.S. PATENT DOCUMENTS

| | | | |
|---|---|---|---|
| 2012/0203569 A1* | 8/2012 | Altman | G06Q 50/22 |
| | | | 705/3 |
| 2018/0261203 A1* | 9/2018 | Zoller | G10L 13/027 |
| 2018/0358117 A1* | 12/2018 | Neagle | G16H 40/63 |
| 2020/0137001 A1* | 4/2020 | Wu | G06F 40/253 |
| 2020/0184278 A1* | 6/2020 | Zadeh | G06F 16/953 |
| 2020/0251098 A1* | 8/2020 | Metallinou | G10L 15/197 |

* cited by examiner

APPARATUS, SYSTEM AND METHOD FOR PREDICTIVE PROCESSING OF ELECTRONIC HEALTH DATA FOR NOTIFICATION SYSTEM

RELATED APPLICATIONS

The present application is a continuation-in-part of U.S. patent application Ser. No. 15/994,880 to Shoenberg et al., titled "Apparatus, System and Method for Secure Processing and Transmission of Data", filed May 21, 2018, the contents of which is incorporated by reference in its entirety herein.

TECHNICAL FIELD

The present disclosure relates to secure computer systems and transmitting information across the computer system to unsecure devices. More specifically, the present disclosure is directed to a notification transmission system that utilizes processor-based predictive modeling to determine notification scheduling.

BACKGROUND

Electronic health record (EHR), or electronic medical record (EMR) computer systems are processor based systems tasked with the systematic collection and processing of patient and population electronically-stored health information in a digital format. These records can be shared across different health care settings, and may be shared through network-connected, enterprise-wide information systems or other information networks and exchanges. EHRs may include a range of data, including, but not limited to demographics, medical history, medication and allergies, immunization status, laboratory test results, radiology images, vital signs, personal statistics like age and weight, and billing information.

Patient portals are healthcare-related online applications that allow patients to interact and communicate with their healthcare providers, such as physicians and hospitals. Typically, portal services are available on the internet and may exist as stand-alone web sites, while other portal applications are integrated into the existing web site of a healthcare provider. Still others are modules added onto an existing EHR/EMR system. Regardless of the specific configuration, patient portals allow patients to interact with their medical information relatively efficiently.

Unlike conventional computer networks, patient portal-based systems must be configured specifically to provide adequate security for authorized users and/or patients. With recent advances in EHR/EMR and patient portal systems, designers have looked to incorporate more notification systems to allow system administrators and users (e.g., patients) to communicate better over the network system. One area that has attracted more interest and research are network-based notification systems for patients, and particularly those that are suited for medicinal applications. Existing notifications are quite rudimentary, and utilize excess network and computative resources. Furthermore, existing notification systems often do not have the necessary security to provide system privacy for patients.

Additionally, most notification systems are based on static notification configurations, where messages are merely transmitted on a fixed schedule, or combine a fixed schedule with modifications based on user responses to the notifications. Such configurations are not optimal, as they unnecessarily use up network bandwidth and take up processor functions that detract from device efficiency. Technologies and techniques are needed to incorporate predictive processing features to notifications to reduce these and other deficiencies.

SUMMARY

In some illustrative embodiments, a system is disclosed for configuring notifications pursuant to a medical regimen for a patient, comprising a portal processor; a communications interface, operatively coupled to the portal processor, wherein the communications interface is configured to receive patient data and patient feedback data associated with the patient; and a portal database, operatively coupled to the portal processor, wherein the portal database comprises system patient data associated with other patients, wherein the portal processor is configured to process a data model for the medical regimen to calculate a baseline notification schedule based on the patient data, wherein the baseline notification schedule comprises content and notification frequency for individual notifications, process the patient data to determine word vectors and embedded vectors from the patient data, execute statistical/predictive processing on the processed patient feedback data to determine a patient characteristic, and modify, via the portal processor, the baseline notification schedule to form a modified schedule for transmission in the system.

In some illustrative embodiments, a processor-based method is disclosed for configuring notifications pursuant to a medical regimen for a patient, comprising: receiving, via a communications interface, patient data and patient feedback data associated with the patient; storing, via a portal database, system patient data associated with other patients, processing a data model for the medical regimen, via a portal processor, to calculate a baseline notification schedule based on the patient data, wherein the baseline notification schedule comprises content and notification frequency for individual notifications, processing, via the portal processor, the patient data to determine word vectors and embedded vectors from the patient data, executing, via the portal processor, statistical/predictive processing on the processed patient feedback data to determine a patient characteristic, and modifying, via the portal processor, the baseline notification schedule to form a modified schedule for transmission in the system.

In some illustrative embodiments, a system is disclosed for configuring notifications pursuant to a medical regimen for a patient, comprising: a portal processor; a communications interface, operatively coupled to the portal processor, wherein the communications interface is configured to receive patient data and patient feedback data associated with the patient; and a portal database, operatively coupled to the portal processor, wherein the portal database comprises system patient data associated with other patients, wherein the portal processor is configured to process a data model for the medical regimen to calculate a baseline notification schedule based on the patient data, wherein the baseline notification schedule comprises content and notification frequency for individual notifications, process the patient data to determine word vectors and embedded vectors from the patient data, execute statistical/predictive processing using a neural network model on the processed patient feedback data to determine a patient characteristic, and modify, via the portal processor, the baseline notification schedule to form a modified schedule for transmission in the system.

BRIEF DESCRIPTION OF THE FIGURES

The present invention is illustrated by way of example and not limitation in the figures of the accompanying drawings, in which like references indicate similar elements and in which.

DETAILED DESCRIPTION

Figure 1:
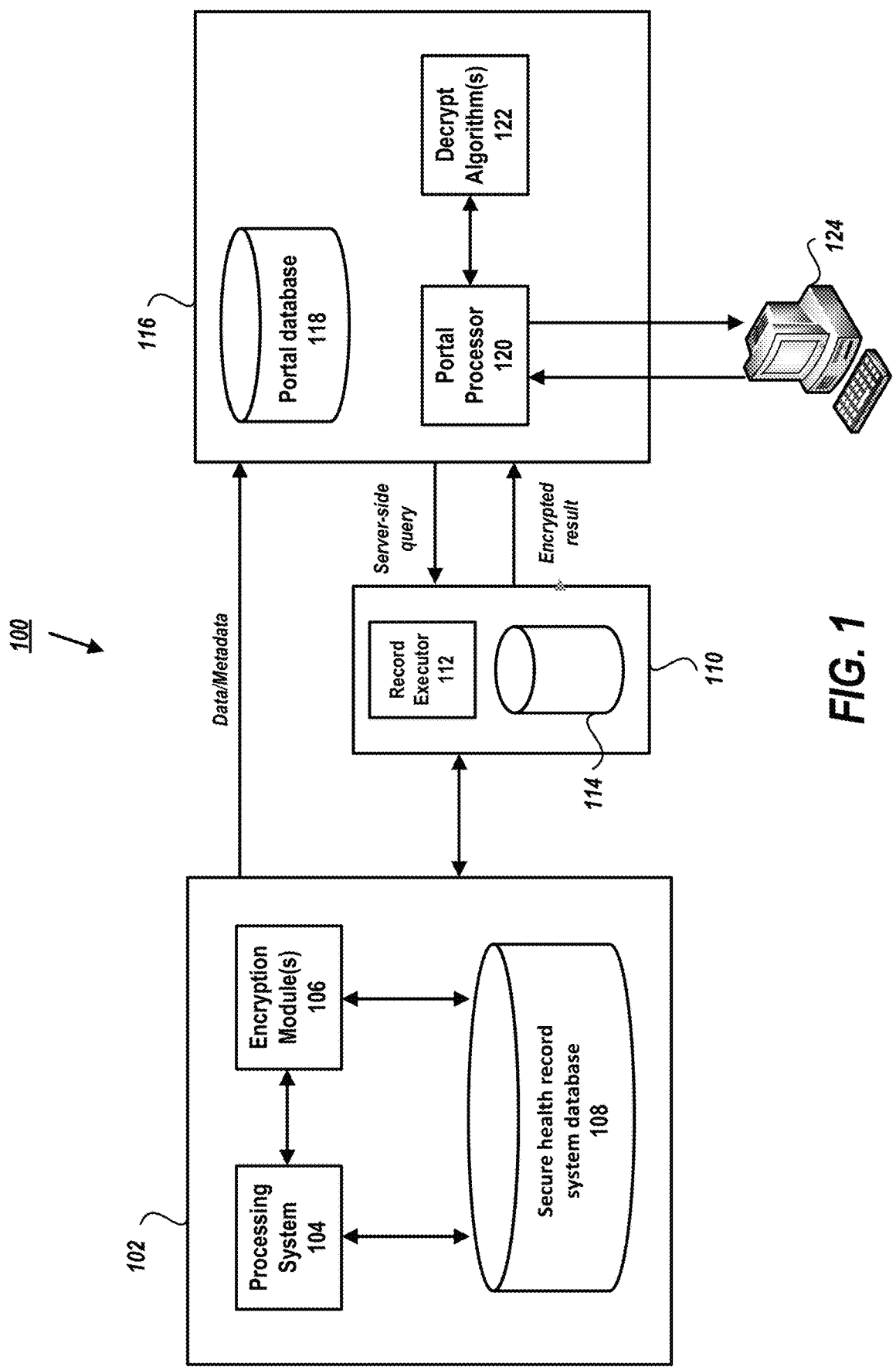
FIG. 1 shows an exemplary Electronic Health Record (HER) system coupled to a server site and a client site configured as a patient portal under an illustrative embodiment.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

It will be understood that the term "module" as used herein does not limit the functionality to particular physical modules, but may include any number of tangibly-embodied software and/or hardware components. In general, a computer program product in accordance with one embodiment comprises a tangible computer usable medium (e.g., standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via Scalable Language ("Scala"), C, C++, C #, Java, Actionscript, Objective-C, Javascript, CSS, XML, etc.).

Turning to FIG. 1, the drawing illustrates a simplified block diagram of an exemplary system 100 comprising a secure health record system (e.g., EHR/EMR) 103 that is configured to communicate with a portal 116 (e.g., patient portal) and a record database server 110. In some illustrative embodiments, record database server 110 may be a stand-alone device, while in other illustrative embodiments, record database server 110 is integrated either with the secure healthcare system 102 or portal 116. Record database server 110 may be located at a health service provider facility, or some other $3^{rd}$ party.

In the example of FIG. 1, secure health record system 102 may comprise of a processing system 104 that is operatively coupled to a secure health record system database 108 that is configured to store data, metadata and other related information. Both the processing system 104 and secure health record system database 108 may be operatively coupled to one or more encryption modules 106, as shown in the figure. Secure health record system 102 may be configured to communicate certain data and metadata to portal 116, where it may be stored in portal database 118. Alternately or in addition, secure health record system 102 may communicate encrypted data to record database server 110, which may store the data in database 114. In some illustrative embodiments, this data may be encrypted (e.g., via encryption module(s) 106). Portal database 118 may be communicatively coupled to portal processor 120 that may use suitable decryption algorithms from module 122 to access data from portal database 118. Once decrypted, the portal processor 120 of portal 116 can communicate data, such as health care data, to a user device 124. It is understood by those skilled in the art that portal processor 120 may be a single processor, configured to perform the functions disclosed herein. In some illustrative embodiments, portal processor 120 may include multiple processors and/or processing apparatuses, with or without associate peripheral devices (e.g., RAM, ROM, data interfaces. etc.).

In some illustrative embodiments a user device 124 (e.g., personal computer, laptop, smart phone, etc.) may communicate with portal 116 to request and receive data. Under an illustrative embodiment, user device 124 may request data (e.g., records) from portal 116. Under an illustrative embodiment, portal 116 may issue a server-side query in response to the request to record database server 110, which utilizes a record executor 112 to retrieve and/or process data from database 114, and provide an encrypted result back to the portal 116, as shown in the figure. In some illustrative embodiments, record database server 110 and/or portal 116 may be provided with executable instructions in order to operate a notification service associated with data stored therein (e.g., 114, 118).

Under an illustrative embodiment, database encryption is used to protect some or all of the data in the system 100 from unauthorized disclosure. The user device 124 may be configured to encrypt records before sending it to the portal 116. In this example, the user may provide data or a query in plain text form, where the data and/or query is translated in the portal 116 into a cipher text form in order to be processed over the encrypted data at the record database server 110. The query result may then be returned in encrypted form from the record database server 110 to the portal 116, where the data is decrypted, filtered and returned to the user device 124. In some illustrative embodiments, the user device 124 may maintain metadata that is necessary for encryption, as well as metadata delivered by the data owner for properly translated the original query and decrypted the result. This encryption scheme assumed that the client had the complete access to the query results.

In some illustrative embodiments, the system 100 may be based on an openEHR framework to allow implementation of interoperable EHRs by using portable vendor-neutral open models and content definitions. Such a configuration may advantageously bring syntactic and semantic interoperability to the EHR environment using a standardized reference model at the technical level and an archetype model at the clinical knowledge level. In these examples, the openEHR framework may be configured as a multi-level modelling paradigm, where in a first modeling level, a common reference information model may define a set of general reusable building blocks (e.g., data types and structures). These structures may be configured to support medical requirements and record management functions, and to ensure that information can be sent and received by systems connected in the EHR network. In a second level, an archetype model may be configured to specify reusable and domain-specific definitions of healthcare concepts are may be captured and modelled. This may be done by using archetypes that, for specific clinical data, constrain and define how the Reference Model building blocks are combined, named, and used in tree-like data structures, which provide an information schema for the clinical data. Above the archetypes, templates may be provided that are based on the archetype model. A template may be defined as a specification that defines a tree of one or more archetypes, where each constrain instances of various reference model types, such as Composition, Section, Entry Subtypes, etc. Thus, archetypes may be provided for data, such as a clinical result (an observation archetype) and SOAP headings (a section archetype), and templates may be used to put archetypes together to form whole compositions in the EHR, e.g., for "discharge summary", "antenatal exam" and so on.

Archetypes may be configured to define re-usable data point and data group definitions and content items that may be re-used in numerous contexts (e.g., systemic arterial blood pressure measurement, serum sodium, etc.). The data points may occur in logical. For example, data points may refer to a group of data items to document an allergic reaction, or the analytes in a liver function test result. Some archetypes may contain a plurality of data points, sometime up to 50 data points or more. A collection of archetypes can be considered a library of re-usable domain content definitions, with each archetype functioning as a governance unit, whose contents are co-designed, reviewed and published.

Each template may be used to logically represent a use case-specific data-set, such as the data items making up a drug side effects, patient discharge summary, prescription regimen, and/or a medical report. A template may be constructed by referencing relevant items from a number of archetypes. A template may be configured with one or two data points or groups from each archetype, or may include more data points. Templates may be defined for GUI screen forms, message definitions and document definitions, and as such, correspond to operational content definitions. In some illustrative embodiments, if data set definitions include pre-defined data points from a library of such definitions, then some or all recorded data (i.e. instances of templates) maybe instances of the standard content definitions.

In some illustrative embodiments, the system 100 may be based on a Health Level 7 (HL7) platform. In the example of FIG. 1, the system 100 may utilize messages using a non-XML encoding syntax based on segments (lines) and one-character delimiters. Segments may be configured to have composites (fields) separated by the composite delimiter. A composite can have sub-composites (components) separated by the sub-composite delimiter, and sub-composites can have sub-sub-composites (subcomponents) separated by the sub-sub-composite delimiter. Each segment may start with a 3-character string that identifies the segment type, and each segment of the message contains one specific category of information. Each message may have a first segment that includes a field that identifies the message type. The message type may then determine the expected segment types in the message, and the segment types used in a particular message type are specified by the segment grammar notation used in the HL7 standards.

Figure 2:
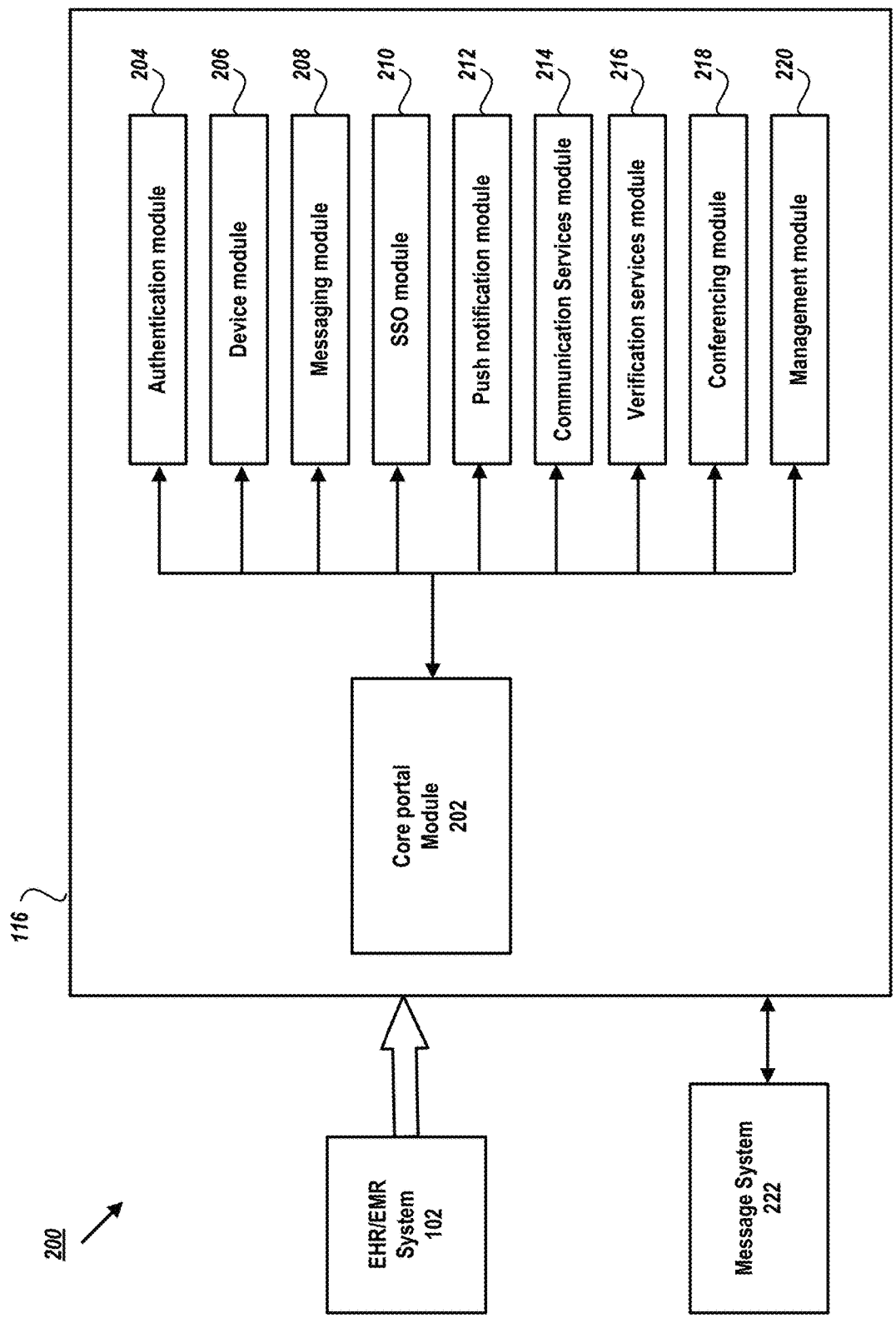
FIG. 2 shows an operating environment for a patient portal system comprising a core portal module, operatively coupled to a plurality of functional modules under an illustrative embodiment.

FIG. 2 shows an operating environment 200 for a portal 116 configured as a patient portal system under an illustrative embodiment. In this example, portal 116, is communicatively coupled to EHR/EMR system 102, similarly to that disclosed above in connection with FIG. 1. Portal 116 may also be communicatively coupled to a messaging system 222 that may be part of a communication service, discussed in greater detail below. Portal 116 may comprise a core portal module 202 that is configured to perform most or all processing functions of portal 116. The core portal module may 202 operate on one or more processing devices (e.g., portal processor 120). The core portal module 202 may be operatively coupled to a plurality of other modules, such as modules 204-220, which may also operate on the one or more processing devices (e.g., 120), or may be distributed among other processors within the portal 116 and/or other suitable regions of the system (e.g., 100).

These modules include, but are not limited to, authentication nodule 204, device module 206, messaging module 208, 3$^{rd}$ party single sign-on (SSO) module 210, push notification module 212, communication services module 214, verification services module 216, conferencing module 218 and management module 220. Authentication module 204 (or "security module") is configured to provide security functions for the system (e.g., 100) and provide encryption and/or decryption functions, among others. In some illustrative embodiments, the authentication may be based on block cipher technology, such as Advanced Encryption Standard (AES), Data Encryption Standard (DES) or RSA. In some illustrative embodiments, an encryption scheme may be utilized, where sub keys are used instead of block ciphers. Further explanation of the authentication techniques utilized herein may be found in FIGS. 2A-2B, below.

Device module 206 may be configured to manage device connections to portal 116. Device module 206 may be configured to translate and/or interpret between different device platforms that communicate with portal 116. Messaging module 208 may be configured to provide messaging to devices (e.g., 124, 506). The messages may be in the form of text, audio, images and/or video and may be transmitted via email, Short Message Service (SMS), Multimedia Message Service (MMS), Enhanced Messaging Service (EMS), Rich Communication Services (RCS), Synchronized Multimedia Integration Language (SMIL), Alexa Voice Service, Google Home Voice Service, or any other suitable format. In some illustrative embodiments, messaging module 208 may interface with an Application Programming Interface (API) to allow various individual and combinations of messaging formats to be communicated. Messaging may typically be performed via one or more communication interfaces (e.g., via communication services module 214) that connects portal 116 to any device or server in network 100. In some illustrative embodiments, messaging module 208 may be operatively coupled with authentication module 204 to allow for encrypted communication.

SSO module 210 may be configured to provide access control of multiple independent, software systems. SSO module 210 may allow a user to log in with a single ID and password to gain access to a connected system or systems without using different usernames or passwords, or in some configurations seamlessly sign on at each system. In some illustrative embodiments, this may be achieved using the Lightweight Directory Access Protocol (LDAP) and stored LDAP databases on (directory) servers. A simple version of single sign-on can be achieved over IP networks using cookies but only if the sites share a common DNS parent domain. In some illustrative embodiments, the system may require authentication (e.g., via authentication module 204) for each application but using the same credentials from a directory server as Directory Server Authentication and systems where a single authentication provides access to multiple applications by passing the authentication token seamlessly to configured applications as Single Sign-On. As different applications and resources support different authentication mechanisms, SSO module 210 may internally store the credentials used for initial authentication and translate them to the credentials required for the different mechanisms. Examples of shared authentication schemes include OAuth, OpenID, OpenID Connect and Facebook Connect. SSO module 210 may be Kerberos-based, smartcard-based, and/or use integrated Windows authentication and/or Security Assertion Markup Language. In some illustrative embodiments, mobile devices may access SSO module 210 as access controllers, where user mobile devices may automatically log them onto multiple systems, such as building-access-control systems and computer systems, through the use of authentication methods that include OpenID Connect and SAML, in conjunction with an X.509 ITU-T cryptography certificate used to identify the mobile device to an access server.

Push notification module 212 may be configured to automatically push messages (e.g., from messaging module 208) to other devices (e.g., 124) in the system 100. Push notification module 212 may be configured to receive messages from message module 208, and may also be equipped with a scheduling algorithm to provide predetermined programming for push notifications. Communication services module 214 may also be communicatively coupled to messaging module 208 to provide communication of messaging. Verification services module 216 may be configured to provide verification services for various medical and patient data, and may be configured to provide multi-level verification services. Verification services model 216 may be a stand-alone module, or may be integrated with authentication module 214. Conferencing module 218 may provide conferencing services for users accessing the portal. Management module 220 may be configured to provide various management services for the portal 116, including, but not limited to billing, finances, insurance, etc.

In some illustrative embodiments, the portal 116 is configured to receive patient medical data, such as individual medical history, current symptoms, biometric data, admission notes, on-service notes, progress notes (SOAP notes), preoperative notes, operative notes, postoperative notes, procedure notes, delivery notes, postpartum notes, and discharge notes. Medical history data may include, but is not limited to surgical history, obstetric history, medications and medical allergies, family history, social history, habits, immunization history and growth chart and development history. In an illustrative embodiment, the system (100) may be configured to process the patient medical data to configure a notification and feedback schedule for users to ensure that users are adhering to a specific medical regimen, and that the regimen is compliant with the patient medical data. At the outset, the medical regimen is manually or automatically created and stored in portal database 118. The patient medical data may be automatically transmitted from the health record system 102, or may be requested from a user via portal 116. Once received, the portal processor 120 may execute the notification algorithm to begin supplying notifications to a user (patient).

In an illustrative embodiment, the notification service executed by portal processor 120, transmits scheduled messages relating to a medication regimen. These messages may be simple notifications (e.g., "reminder to take medicine at 4:00 PM"), or may include interactive messages (e.g., "it is now 4:00 PM—did you take your medicine? (Y|N)"). The interactive messages may comprise feedback and compliance entries for the user to input. These feedback and compliance entries may contain questions regarding the physical, physiological and/or psychological condition of the user during the medication regimen (e.g., "how are you feeling (enter all that apply)? fine, dizzy, hungry, sleepy, alert, nervous", etc.). The responses received from the user may be used by a compliance algorithm in core portal module 202 to automatically adjust the message schedule and/or content. Alternately or in addition, the core portal module 202 may grant access to others for the notification service, and also may allow others access to the patient medical data.

For example, if the data received from the user is approaching or outside the threshold(s) of the medication regimen, often times it may be necessary to add others to the notification system, to receive information and/or allow others to participate in observing the medication regimen, together with, or independently of, the user (patient). For example, if a user is not responding, taking medication, and/or experiencing side effects, the portal 116 may be configured to produce additional messaging to others, such as a primary or secondary service provider, clinician, nurse, relative, friend, etc. However, given the aforementioned security requirements for medical data, there may be instances where a user does not want each and every member of the group to see or have access to specific medical data (or any medical data). In such cases, it is often cumbersome and/or impractical to use a traditional encryption scheme to grant access, particularly in cases where the notifications occur in real time, and refer to the same body of medical data.

Figures 2A, 2B:
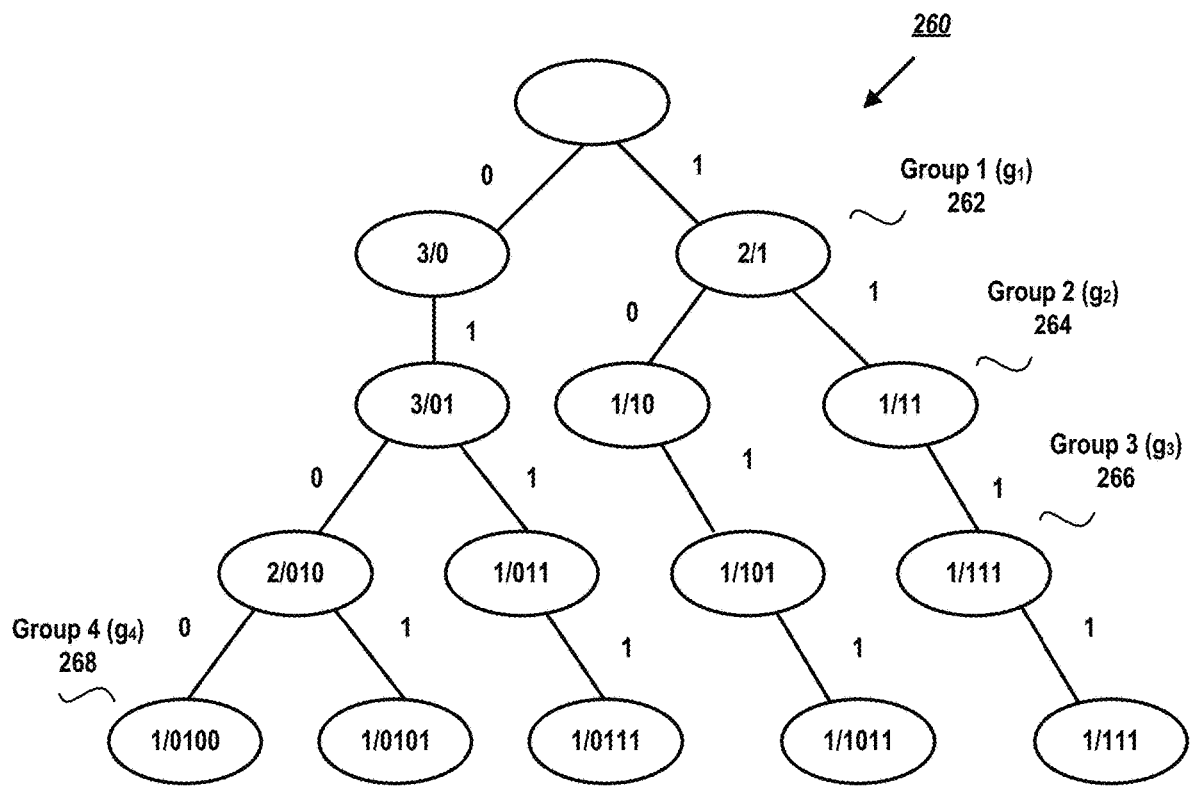
FIG. 2A shows an access matrix for describing access policies to patient medical data under an illustrative embodiment.
FIG. 2B shows a binary tree that may be configured to correspond to the access matrix of FIG. 2A under an illustrative embodiment.

Accordingly, the system 100 may be configured to utilize an encryption technique that groups users into levels of access and utilizes cryptographic sub keys to provide different levels of access for each group. In some illustrative embodiments, for each relation $R(A_1, A_2, \ldots, A_n)$, the data owner (e.g., user and/or operator of portal 116) stores encrypted relation $R^S$ (etuple, $A_1^S, A_2^S, \ldots, A_n^S$) on the server (e.g., portal database 118), where the attribute etuple is the encryption form of a record using the encryption scheme with sub keys. In order to protect the data, the data owner may describe the access policies to the data by using an access matrix 250 by row, as illustrated in FIG. 2A. The access matrix 250 by row (A) may be configured to have the number of columns equal to the number of row of the considering relation, and number of row equals to the number of users in the system. As an example, $A[i, j]=1$ if user i is allowed to access to the column j; otherwise, the value is set to 0. The columns of A may be grouped into disjoined row categories ($r_1$-$r_5$), and the rows of A may be grouped (262-268) into disjoined user groups ($g_1$-$g_4$). Each row category may comprise rows on which all the users have the same access permission. Each user group may be comprised of users that have the same access permission to the rows ($g_1$-$g_4$) of the considering relation.

In some illustrative embodiments, a binary tree may be formed (see FIG. 2B, 260) that corresponds to the access matrix after formation to calculate the number of keys that will be distributed to each group of users. The keys assigned to the user group at the leaf-level of the binary tree are used to encrypt/decrypt the data. The keys granted to the users at the non-leaf level of the tree must be able to be used for deriving to the necessary decryption keys for reading the data with granted permission. An illustrative configuration is provided below in TABLE 1:

TABLE 1

| User Group | Keys Held by Each Group | Derivable Keys |
| --- | --- | --- |
| $g_1$ | $k_1$ | $k_{111}, k_{1011}$ |
| $g_2$ | $k_{01}, k_{11}$ | $k_{0111}, k_{111}, k_{0101}, k_{0100}$ |
| $g_3$ | $k_{011}, k_{101}, k_{111}$ | $k_{0111}, k_{1111}, k_{1011}$ |
| $g_4$ | $k0_{111}, k_{1111}, k_{1011}, k_{0101}$ | |

The data owner may selectively restrict access to the more sensitive columns by giving out only the sub keys corresponding to the columns that the user(s) have access permission.

If the users in a group G have different access privileges to different columns of a row category R, the data owner provides the access policies using an access matrix, referred to as an access matrix by column. The number of rows of this matrix may equal the number of subgroups of users in the group G and the number of columns equals to the number of groups of columns in R with different access authorizations. As described above a binary tree structure corresponding to this access matrix may be configured by column. In this example, each subgroup of users holds a number of some sub keys. Appropriate sub keys are communicated to users by the data owner via a secure channel. These sub keys may be used for deriving the encryption/decryption sub keys in order to access the columns with the granted permission. The derivation may be done by using a one-way function which takes in input an integer and outputs an integer for none-leaf level user groups, or by using the one-way hash function which takes an integer as input and outputs a prime for leaf-level user groups. Using this configuration, data, such as patient records and/or medical notification messages, are protected from unauthorized disclosure and they can restrict access to the more sensitive columns of the data being shared.

For data encryption, a Chinese Remainder Theorem (CRT) may also be utilized for encrypting a database. In EHR systems (e.g., 100), the convenience for a user to access data at a service provider is important, therefore an encryption scheme requiring less keys held by each valid user may be preferable. Under an illustrative example, assuming there are m records or messages in a given relation r consisting of n fields. The $i^{th}$ record of r is of the form $x_i=(x_{i1}, x_{i2} \ldots x_{in})$. Using $C_i$ as the cipher text of $x_i$, the encryption procedure may be expressed as follows:

$$C_i = \sum_{j=1}^{n} e_j(r_{ij} \| x_{ij}) \bmod D, \text{ for } i = 1, \ldots, m$$

and $D = \prod_{j=1}^{n} d_j$, where $j=1,2,\ldots,n$ where $e_j=(D/d_j)b_j$, and $b_j$ is the multiplicative inverse of $(D/d_j)$ with moduli $d_j$. Each subkey $d_j$ is a prime such that $a_{ij}<d_j$, $a_{ij}=(r_{ij}\|x_{ij})$, where $\|$ is the concatenation, $r_{ij}$ is the random value for the field j that is used for preventing attacks originated from using CRT. $d_j$ $j=1, \ldots, n$, may be considered the reading subkey for the field $j^{th}$. The decryption procedure may be expressed as $(r_{ij}\|x_{ij})=C_i \bmod d_j$, $j=1,\ldots,n$. By discarding the random bit $r_{ij}$, one can obtain the $j^{th}$ field data $x_{ij}$ of the record $i^{th}$.

For key derivation, each key in the sub key encryption scheme may include multiple different sub keys ($d_{i1}$, $d_{i2}, \ldots, d_{in}$). Each subkey $d_{ij}$ of a key granted to the users at the non-leaf level $SC_i$ of the binary tree is a large integer. In the case when $SC_i$ is at the leaf level of the tree, each subkey of $SC_i$ is a prime for properly using the CRT. The key of security class $SC_j$, which is an immediate child of $SC_i$, may be computed by $(f_{j1}(d_{i1}), f_{j2}(d_{i2}), \ldots, f_{jn}(d_{in}))$, where each fji may be configured as a one-way function. In this example, a plurality of functions for $f_{ji}$ may be used, where a first function is the one-way function that takes an integer as an input, and outputs an integer. This function may be used for deriving keys of the non-leaf level security class. Another function may include a one-way function that receives an integer as the input but outputs a prime, This function may be used for deriving keys for the leaf-level security class.

For constructing a one-way hash function that receives an integer as an input and outputs a prime, users having same privileges may generate the same keys at different times for deriving keys to access specific data, and/or allow users to message at different security levels. Assuming that $$(n-1) = F \times R = \left( \prod_{i=1,\ldots,s} p_i^{a_i} \right) \times R,$$

where $R<\sqrt{n}$, and an integer b such that $b^{n-1}\equiv 1 \pmod{n}$ exists and gcd $$\left( b^{\frac{n-1}{p_i}} - 1, n \right) = 1,$$

where $i=1, 2, \ldots, s$. Accordingly, n would output as a prime.

Assuming a seed s, generating a prime of d digits, a value Q may be generated that includes (d−2) digits using consecutive hash values of seed s. This may be expressed as $Q=h(s)\| \ldots \| h(s)$, where $\|$ is the concatenation operator. Next, the greatest R is determined such that $(R<Q)$ and $(1+RQ\equiv 1 \pmod{6})$. If $p=RQ+1$ is a pseudo-prime with base 2 and 3, then the system returns integer p. Next, R is set to R+6 and the process then returns to determining the greatest R, and so on. For a key deriving function, h may be assumed as a one-way hash function such that $h:Zn \rightarrow H$ For key storage and access control, each user may own some sub keys that are used for accessing or deriving to the necessary sub keys to access the fields authorized for access. For key management, suppose that a user i is granted n sub keys, each subkey may be assigned to a public prime number $p_j$, for $j=1, 2, \ldots, n$. Next, the secret master key MK, may be computer by CRT for user i:

$MK_i=d_j \bmod p_j$ for some j, $1 \leq j \leq (n+1)$, where $d_j$ is the reading subkey, $d_{n+1}$ and $p_{n+1}$ are the random secret key and the prime assigned to this subkey which are used for preventing users from colluding to disclose the secret master key of user i. During operation, user i keeps only the secret master key $MK_i$. To read the subkey $j^{th}$, user i computes $d_j=MK_i \bmod p_j$ to get subkey $d_j$.

The configurations discussed above may be advantageously used in a portal (e.g., 116), particularly one operatively coupled to a EHR/EMR, as the techniques are particularly suited for large amounts of sensitive material that may require different levels of access. In some illustrative embodiments the encryption security may be run from the secure healthcare system 102. By designating levels of access to subgroups (e.g., $g_1$=patient/doctor/specialist, $g_2$=nurse/pharmacist, $g_3$=family members, $g_4$=friends), the notifications can be controlled using the aforementioned sub keys. In addition, notification alerts may be made specific to user groups by using the sub keys.

Figure 3:
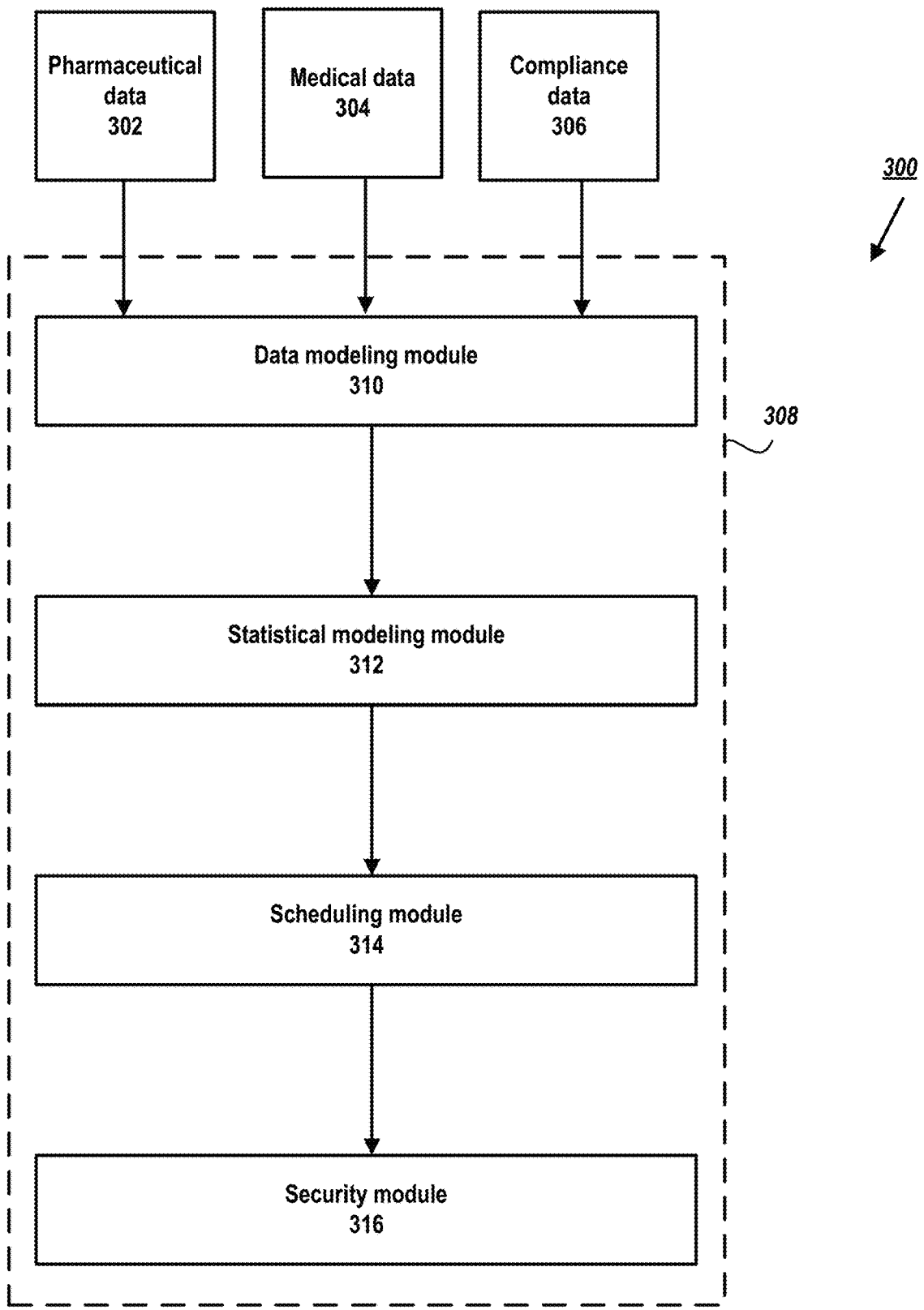
FIG. 3 shows an operating environment for a processing apparatus in a portal system to receive data and perform modeling and security processing under an illustrative embodiment.

FIG. 3 shows an operating environment 300 for a processing apparatus in a portal system to receive data and perform modeling and security processing under an illustrative embodiment. In this example, patient medical data is provided in the form of pharmaceutical data 302, medical data 304 and compliance data 306. The patient medical data may be provided from secure healthcare system 102, portal 116, or a combination of both. Pharmaceutical data may provide data relating to, but not limited to, drug type, dosage, interacting drug combinations, or any other drug-related information currently known in the art. Medical data 304 may include any form or type of patient medical data described herein or otherwise known in the art. Compliance data 306 comprises actual and/or statistical data relating to one or more drugs for the medical regimen being monitored by the system. Actual compliance data comprises a history of data provided by the user (patient) during a current or previous drug regimen, and compliance relating to a specific regimen (e.g., whether user took proper dosages ad proper times). The actual compliance data may also comprise timing data that indicates whether a user historically responds in a timely manner at regular intervals, and/or whether certain responses are non-compliant or late at specific periods of time. Additionally, the compliance data 306 may include behavioral compliance data indicating whether a user is complying with restrictions (e.g., food, alcohol, etc.) relating to a medical regimen.

Patient medical data 302-306 is then input into a notification module 308 that may be executed on core portal module 202 of portal processor 120. Notification module 308 may be configured to incorporate some or all of modules 204-220. In some illustrative embodiments, notification module 308 may include a data modeling module 310 that processes the patient medical data 302-306 to form a user-specific model for transmitting notifications relating to a medical regimen. The patient medical data 302-306 may also be transmitted to statistical modeling module 312, which processes the data to provide a statistical model for the medical regimen, based on stored data relating to members of the general public having the most common characteristics with that of the user. Scheduling module 314 may then combine the models from 310 and 312 to formulate a global model that is specific to the user, while incorporating data from statistical module 312 to supplement incomplete or missing data. Once a global model is formed, the scheduling module 314 schedules a notification regimen that comprises a plurality of reminders, questionnaires, and the like to be transmitted to a user device (e.g., 124) on a determined schedule. Additionally, scheduling module 314 may draw from a pre-stored database to determine specific feedback required from the user during the medical regimen. Depending on this feedback, the operating environment 300 may include a feedback loop into the compliance data 306 in order to update the compliance data and re-run the data modeling module 310 at predetermined intervals of time.

Once the scheduling module 314 computes a schedule, the data is provide to security module 316. In an illustrative embodiment, security module 316 may receive group assignment for data access (e.g., $g_1$-$g_4$) and formulate sub key encryption described above for the various notification messages. Security module 316 may also provide links or tags, consistent with each groups assignment, that allows each respective group to view medical data relating to the user in accordance with their level of access.

Figure 4:
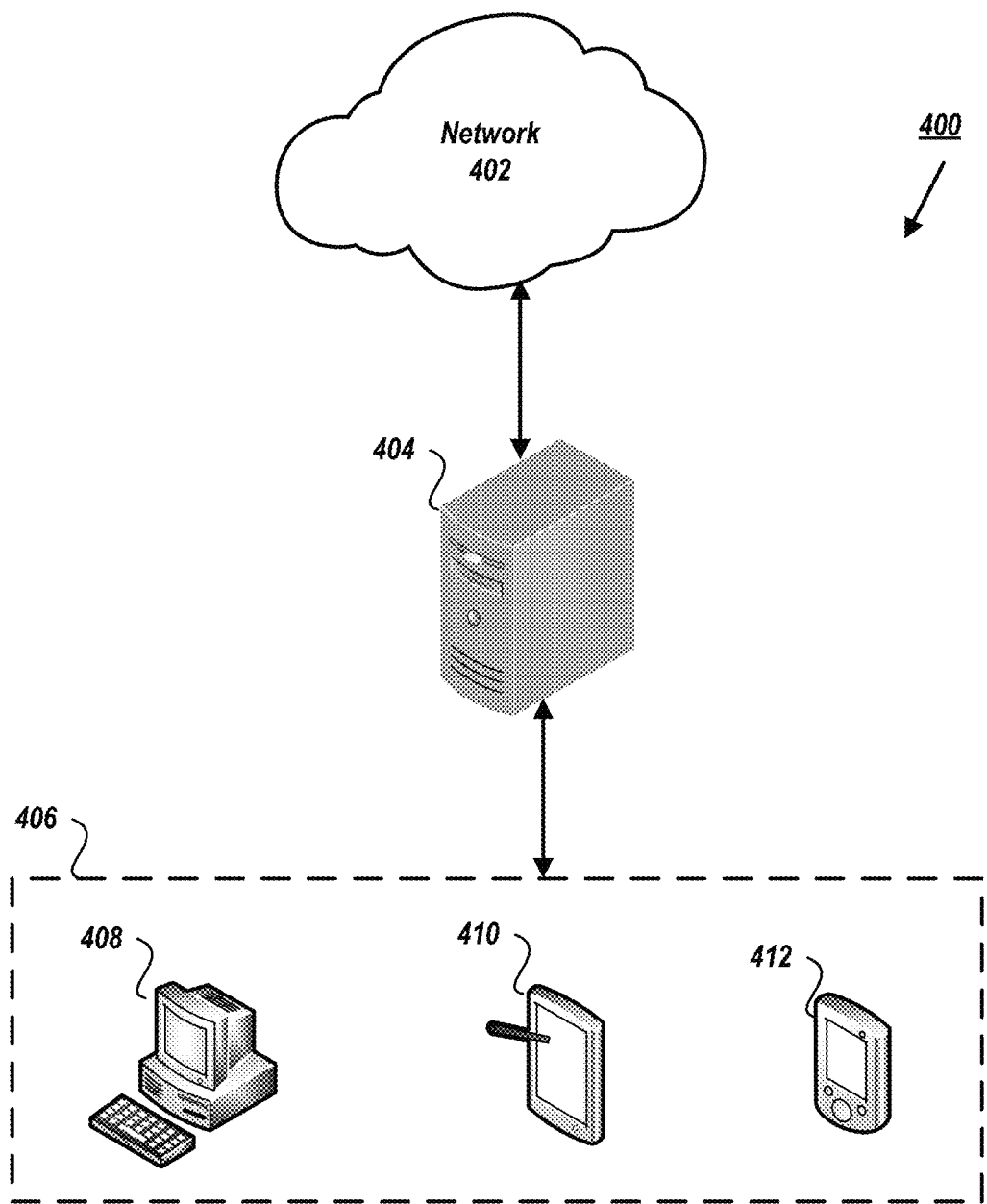
FIG. 4 shows a simplified block diagram for a computer network hardware arrangement for performing any of the functions disclosed in the present disclosure under an illustrative embodiment.

FIG. 4 shows a simplified block diagram for a computer network hardware arrangement 400 for performing any of the functions disclosed in the present disclosure under an illustrative embodiment. Computer network hardware arrangement 400 comprises a network 402 that may include one or more servers. In one embodiment, network 402 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of network 402 may be configured to use any one or more, or combination, of communication protocols to communicate such as, for example, a wired network communication protocol (e.g., TCP/IP), a wireless network communication protocol (e.g., Wi-Fi®, WiMAX), a cellular communication protocol (e.g., Wideband Code Division Multiple Access (W-CDMA)), and/or other communication protocols. As such, the network 402 may include any number of additional devices, such as additional computers, routers, and switches, to facilitate communications. Network 402 may include health record system 102 and processing system 104, among others.

In this example, network 402 is communicatively coupled to server 404 that comprises portal 116. It should be understood by those skilled in the art that, while only one server (404) is illustrated, two or more networked servers, configured similarly as network 402 are contemplated in the present disclosure. Server 404 is configured to communicate with one or more user devices 406 that may include a personal computer 408, tablet 410, and/or smart phone 412. Those skilled in the art will recognize that other devices, such as a home assistant (e.g., Alexa™) or internet of things (IoT) devices are also contemplated in the present disclosure. During operation, notifications may be provided to an account, linking multiple devices (408-412) and allowing users to respond and to provide feedback. In some illustrative embodiments, all of the devices linked to the account may be registered as a group (e.g., $g_1$-$g_4$) for security and encryption purposes. In other illustrative embodiments, only specific devices may be linked to a group allowing access to medical data.

Figure 5:
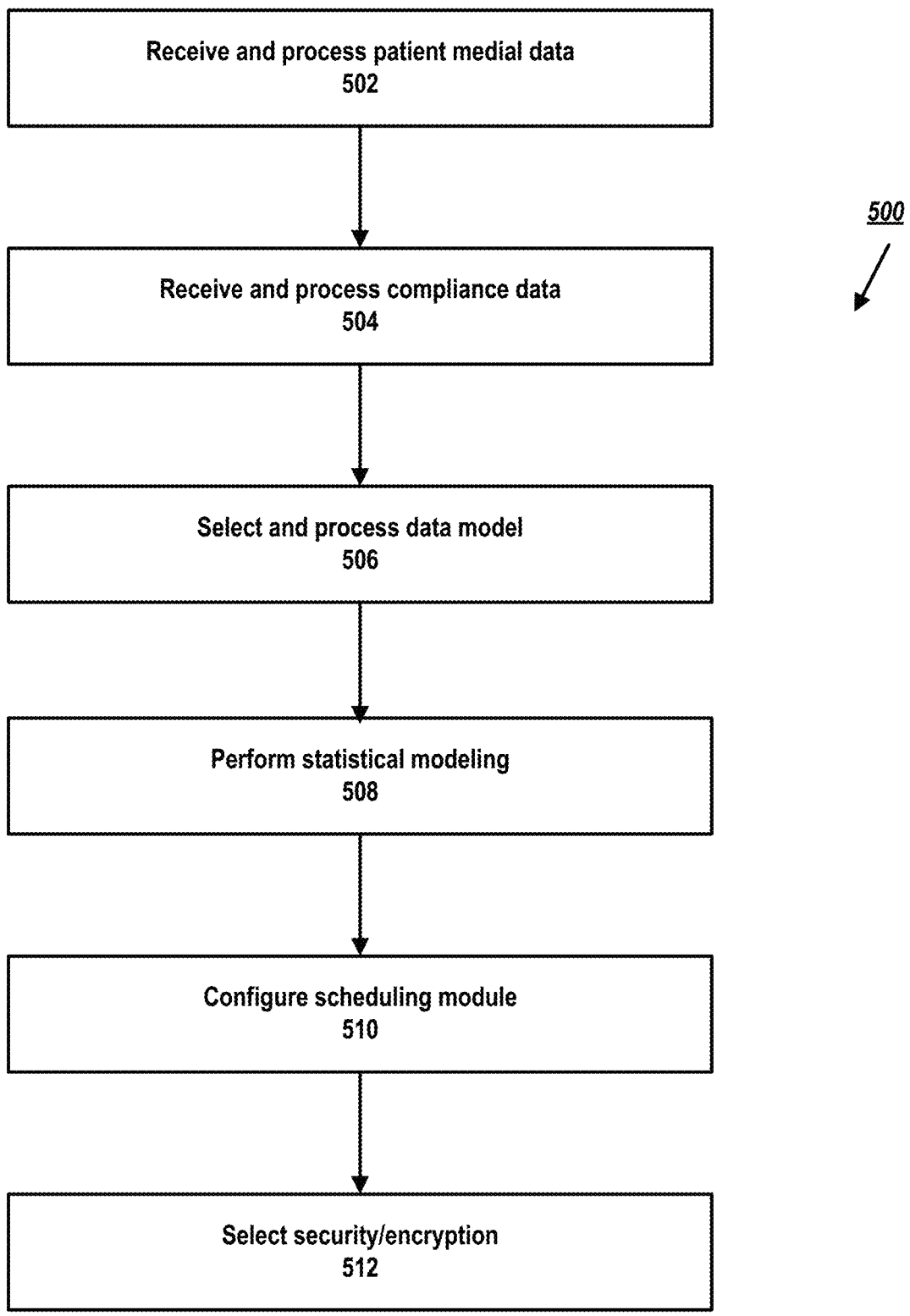
FIG. 5 shows a process for receiving medical data and compliance data, wherein data modeling and statistical modeling is performed for notification transmission that is subject to scheduling and security processing under an illustrative embodiment.

FIG. 5 shows a process 500 for securely transmitting medical notification messages under an exemplary embodiment. In block 502, the portal processor 120 receives and processes patient medical data, described above in connection with FIG. 5. In block 504, the portal processor 120 similarly receives and processes compliance data associated with the medical data. In block 504, the portal processor 120 may additionally receive feedback compliance data in which the portal processor 120 uses to update the compliance data and proceed to block 506 in which a data model is processed and selected. In block 508, statistical modeling is performed as described above and combined with the data model from block 506 to form a global model specific to a user for a medical regimen. In block 510 the portal processor 120 configured the scheduling module to determine the timing and content of the notification messages to be transmitted, and the responses to be received, during the course of the medical regimen. In block 512 user groups for the notification system, in addition to the user, are formed to provide the sub key encryption and data access discussed above.

In an illustrative embodiment, group encryption level and security class for block 512 may be formed using an access matrix, such as the one described in connection with FIG. 2A. The access matrix may be received as an input, and the number of keys that will be used by the data owner to encrypt the database and to distribute to each user group is outputted from portal processor 120. The aforementioned security mechanisms are then used to manage the keys. The users at a security class that is not the leaf-level of the binary tree will use the granted keys to derive all the necessary keys for accessing the granted data. For example, 5 user groups with 5 resource categories would result in an input matrix for constructing the binary tree having the size of 5×5. In some illustrative embodiments, the access matrix may be regenerated if there are at least two user groups having the same capability or two resources on which the users having the same privileges. Once the binary tree is constructed for the matrix, keys are assigned to each group. Keys comprising multiple sub keys indicate that a relation has multiple attributes equaling the number of sub keys. Each key k, assigned to the non-leaf security class $SC_i$ may be configured in the form $(k_{i1}, k_{i2}, k_{i3})$ where kij is an integer. Each key assigned to leaf-level security class $SC_j$ has each sub key issued as a prime. The key derivation process is then performed using a one-way hash function.

Figure 6:
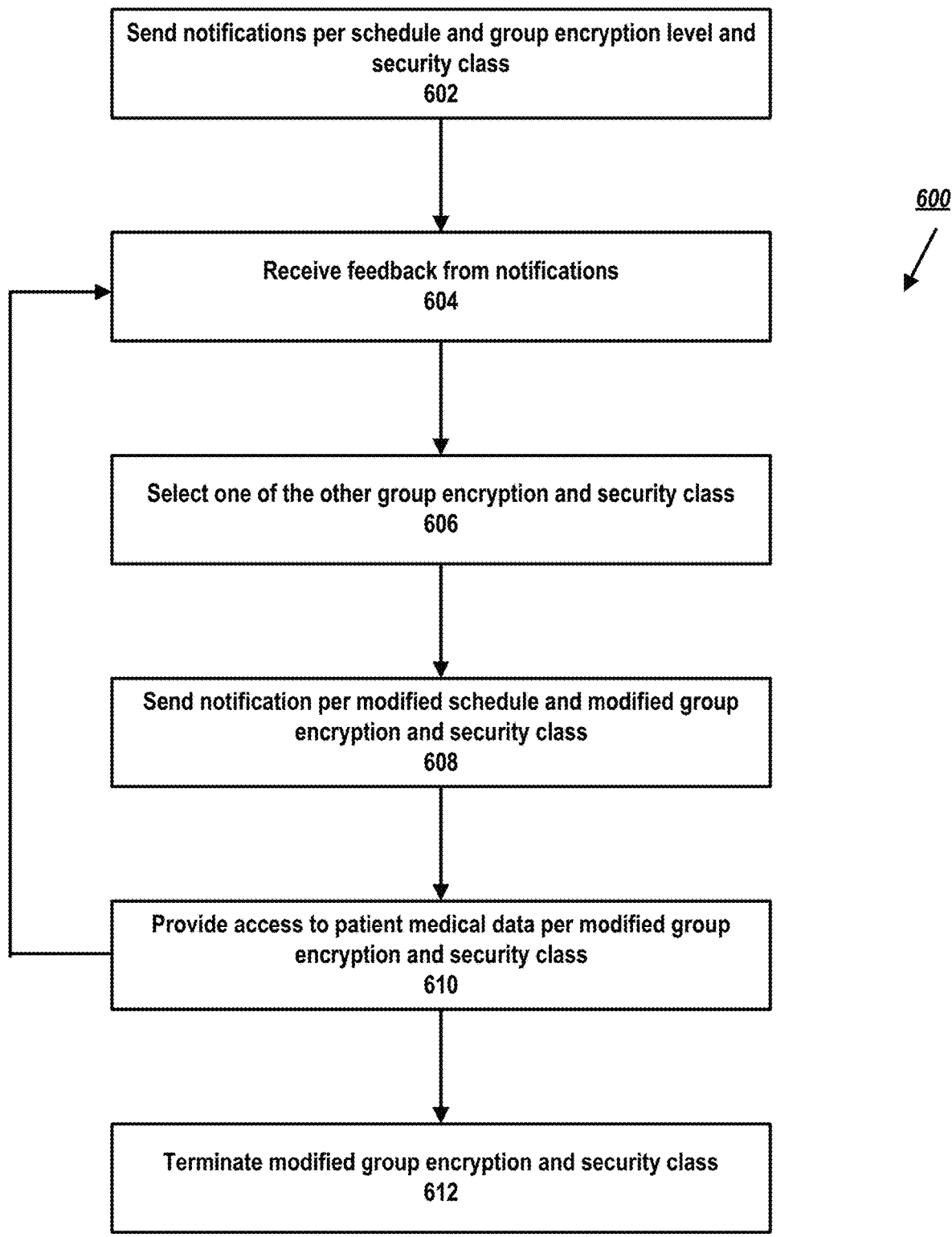
FIG. 6 shows a process for providing secure notification and access under an illustrative embodiment.

Turning to FIG. 6, a process 600 for applying secure notifications to a system (e.g., 100) is disclosed under an illustrative embodiment. In this example, in block 602, the process sends notifications per the determined schedule using the pre-determine group encryption level and security class. Block 602 may be performed similarly to blocks 510-512, as described above in connection with FIG. 5. In block 604, the system (e.g., 100) receives feedback from the users from the notifications. In some illustrative embodiments, the feedback may be specific to each notification, or may alternately or in addition be based on groups of multiple notifications. Based on the feedback received in block 604, the system (e.g., 100) may select one or more of the other group encryption and security class member in block 606 and sends notifications per the modified schedule and modified group encryption and security class in block 608. The schedule may be modified in the sense that sub keys for a different group level (e.g., g 2 keys are provided or activated in addition to $g_1$ keys) are provided for each subsequent notification, thus allowing a larger group to see the notifications. The schedule may also be modified by the content provided in the notifications. For example, once a new group level is added, additional message content may be added into the notifications (e.g., modifying the original notifications and/or providing layered "group 1" and "group 2" messaging that may be separate or combined with each notification).

In block 610, the system (e.g., 100) may provide access to medical data per modified group encryption and security class as part of the messaging. This access may be provided in the form of a link, or may be the actual medal history/data from an EHR. The access may be provided via the same sub keys that granted access to the notifications. The process 600 may then loop back to block 604, where additional user feedback from the notifications is provided, and, depending on the additional feedback, another group (e.g., $g_3$) may be added to the notification, and the processes of clocks 606-610 would be repeated. Alternately, a previously selected group (e.g., $g_2$) in block 606 may be removed, depending on the received feedback (e.g., indicating that the user is now in compliance). This configuration advantageously removes unnecessary parties from the notification and minimizes the exposure of sensitive data. Once the processes of blocks 604-610 have be executed according to the medical regimen, the process 600 terminates modified groups encryption and security classes for all users.

The technologies and techniques disclosed herein provide a flexible and secure way to allow multiple users to be involved in medicinal/pharmacological notifications of a medical regimen. Unlike conventional systems, the present systems and methods minimize risks of inadvertent disclosure of sensitive information, and allows for additional users to be brought in on an ad-hoc basis, depending on there security classification group.

Figure 7:
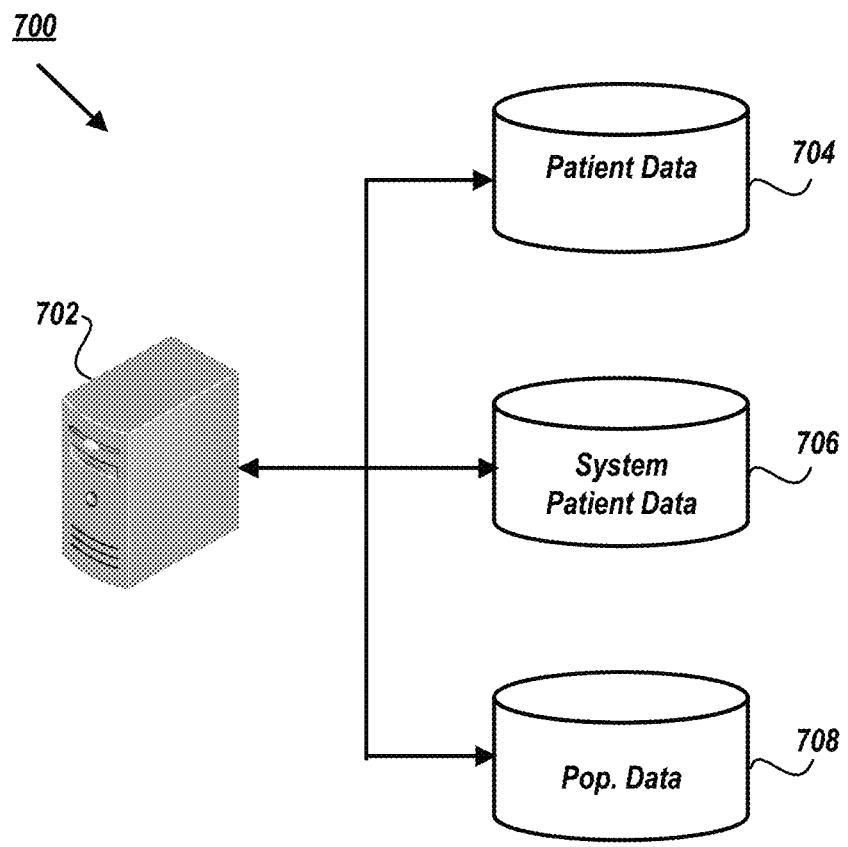
FIG. 7 shows a simplified portion of a system for performing statistical and predictive processing of data under an illustrative embodiment.

Turning now to FIG. 7, the drawing shows a simplified portion of a system 700 for performing statistical and predictive processing of data under an illustrative embodiment. The system may be incorporated as part of systems 100 and/or 400 and may be used as a part of statistical modeling module 312 shown in FIG. 3. In this example, server 702 is operatively coupled to patient data database 704, system patient data database 706 and population data database 708. Server 702 may be configured to receive data from any or all of databases 704-708 and perform statistical and/or predictive processing as described herein. As used herein, statistical processing refers to the processing, manipulating or classifying statistical data into various categories with the object of producing statistics. Predictive processing refers to the processing of statistical data and/or other data to enable machine learning to "learn" (e.g., progressively improve performance on a specific task) with data, without being explicitly programmed.

Patient data database 704 may include data associated with a specific patient, and may include patient demographic data (e.g., age, sex, ethnicity, etc.), patient medical data and prescription data (e.g., medical condition(s) and history, prescription history, etc.) and patient personal data (e.g., interests, hobbies, activities, etc.). System patient data database 706 may include the same data as that stored in patient data database 704, but includes the data for each of the other patients registered in the system. Population data database 708 may include data associated with a general population, and may similarly include the same data as stored in databased 704, but may also include other data relating to a populace. For example, population data database 708 may be configured as a Census Bureau database. In another example, population data database 708 may be a commercially-available $3^{rd}$-party server (e.g., Facebook, Google, Twitter, etc.) that collects user data pursuant to a service. Those skilled in the art will understand that databases 704-708 may be configured as individual stand-alone servers, or may be configured as multiple servers and/or a cloud server configurations, depending of the specific needs of the system 700 user.

Figure 8:
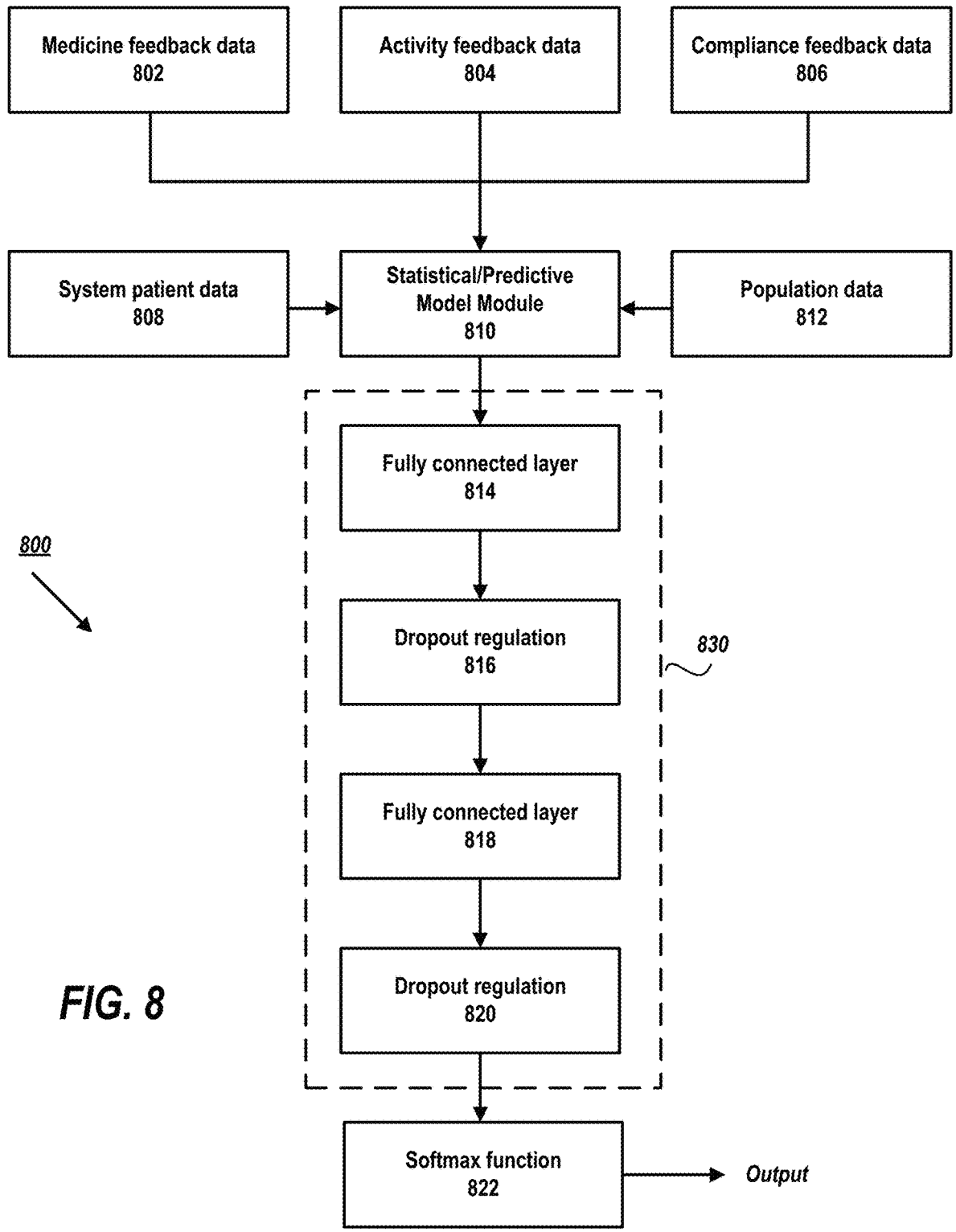
FIG. 8 shows an operating environment for performing statistical and predictive processing of data of the system of FIG. 7 under an illustrative embodiment.

FIG. 8 shows an operating environment 800 for performing statistical and predictive processing of data of the system of FIG. 7 under an illustrative embodiment. In this example, a statistical/predictive model module 810 may begin operation by loading current data stored in patient data database 704, discussed above in connection with FIG. 7. In some illustrative embodiments, statistical/predictive model module 810 may begin engaging in statistical/predictive processing, discussed in greater detail below, based solely on this data. In some illustrative embodiments, statistical/predictive model module 810 may receive additional data from any or all of system patient data 808, which corresponds to data stored in system patient database 706, as well as population data 812, which corresponds to data stored in population data database 708. In some illustrative embodiments, the operating environment 800 of system 700 may additionally receive feedback data (802-806) from the patient that may be used in statistical/predictive model module 810.

Medicine feedback data module 802 may include data that is received in real time from a patient device (e.g., 408-412) relating to medications, other than the medications that are the direct subject of the regimen, that are being taken during the course of a medical regimen. The medications may include other prescription drugs and/or vitamins and/or supplements. For example, if a system (e.g., 700) is configured for a medical regimen for drug "A", the patient may enter medicine feedback data 802 relating to other prescription drugs (e.g., drug "B"), over-the-counter drugs (e.g., ibuprofen) or vitamins/supplements (e.g., niacin, turmeric capsules) that the patient has taken since the beginning of the regimen. Activity feedback data 804 may include physical activities (e.g., running, walking) that are undertaken by the patient during the course of the medication regimen. Compliance feedback data 806 my include data pertaining to the patient's compliance with the medication regimen. This compliance may include data indicating whether or not the patient took the medication(s) in a timely manner, as provided in the initial notification schedule. In some illustrative embodiments, the feedback data (e.g., 802-806) may be provided by input from an interactive dropdown menu being executed on the software on a user's device (e.g., 408-412). In some illustrative embodiments, the feedback data may be provided by an interactive word cloud that executes on the user's device to receive input. In some illustrative embodiments, the feedback data may be text data inputted from the user's device.

Once the data (e.g., 802-808, 812) is received in the statistical/predictive model module 810, the operating environment 800 loads a statistical/predictive model for machine learning to determine if the notification schedule requires modifications. In some illustrative embodiments, the statistical/predictive model module 810 is based on a neural network model. More specifically, statistical/predictive model module 810 may be configured as a long short-term memory (LSTM) model that may process each of the data (e.g., 802-808, 812) to predict if modifications are needed in the notification scheduling. In one example, the feedback data may be represented as IDs, strings or one-hot vectors, and natural language processing (NLP) may be executed with the representation of words. In addition, embeddings may be used to represent the words. Embeddings have the advantage of being dense and more computationally efficient, with the number of features being constant, regardless of the number of feedback entries. Additionally, embeddings may provide semantic meaning to the representation of the feedback entries. In this example, each feedback entry (and/or data from 808 and/or 812) may be represented as a point in a multidimensional plane, which place them at a distance of the other entries, thus providing relations of similitude and significance between them.

Given a sequence of feedback entries $S_{fe}=[e_1, e_2, e_3, \ldots e_{le}]$ where e represents feedback entries and $l_e$ is the sequence length and $e_i \in \Re^{d_e}$ indicates the feedback data entry vector of the $i^{th}$ entry in the sequence, a context may be formed of $e_i$ where $Context(e_i)=[e_{i-n}, \ldots, e_{i-1}, \ldots, e_{i+1}, \ldots, a_{i+n}]$, and 2n is configured as the context window. A probability may be configured as $p(e_i Context(e_i))$ to be the probability of the $i^{th}$ entry of the sequence for feedback entry $e_i$. The target of a model used to create embeddings may optimize the log maximum likelihood estimation as follows $$L_e(MLE) = \sum_{e_i \in S} \log p(e_i Context(e_i))$$

The disclosed configuration may be implemented using a suitable word embedding software algorithm. Generally speaking, language modeling and feature learning techniques in natural language processing (NLP) where words or phrases from the vocabulary are mapped to vectors of real numbers. Conceptually it involves a mathematical embedding from a space with one dimension per word to a continuous vector space with a much lower dimension. One exemplary model is Word2vec, that utilizes multi-layer neural networks that are trained to reconstruct linguistic contexts of words. Word2vec may take as input a corpus of text to produce a vector space, typically of several hundred dimensions, with each unique word in the corpus being assigned a corresponding vector in the space. Word vectors may be positioned in the vector space such that words that share common contexts in the corpus are located in close proximity to one another in the space. Embedding vectors created using the Word2vec algorithm have certain advantages over other algorithms, such as latent semantic analysis.

In some illustrative embodiments, Word2vec can utilize either of two model architectures to produce a distributed representation of words: continuous bag-of-words (CBOW) or continuous skip-gram. In the continuous bag-of-words architecture, the model predicts the current word from a window of surrounding context words. The order of context words does not influence prediction (bag-of-words assumption). In the continuous skip-gram architecture, the model uses the current word to predict the surrounding window of context words. The skip-gram architecture weighs nearby context words more heavily than more distant context words. Generally speaking, CBOW may be used for faster processing applications, while skip-gram is more processor-intensive, but tends to process infrequent words better. A Word2vec model can be trained with hierarchical softmax and/or negative sampling. To approximate the conditional log-likelihood a model seeks to maximize, the hierarchical softmax method uses a Huffman tree to reduce calculation. The negative sampling method, on the other hand, approaches the maximization problem by minimizing the log-likelihood of sampled negative instances. Hierarchical softmax may be used to better process infrequent words, while negative sampling may be used to better process frequent words and low dimensional vectors. Implementations may be accomplished using any of C, Java/Scala, Python (TensorFlow), Python (Gensim), or C #programming languages. Word2Vec implementation in Gensim (or other suitable vector-space modelling library) to calculate the embedding values for each entry in the dataset. Each entry may be represented with a vector of multiple float values (e.g., 20-60). In some illustrative embodiments, the values may be directly entered into a model. In other illustrative embodiments, an embedding layer may be used as the input to the model. The embedded layer may be incorporated into the statistical/predictive model module 810 in one embodiment. The embedded layer may be configured to store the procedural information on how to transform an entry ID to its embedding. Including this layer may provide improved training with the rest of the model and enable fine-tuning of the embedding values to a current task to improve general accuracy of the model.

As mentioned previously, an LSTM model may be utilized in 810 under an illustrative embodiment, utilizing a layer size of 512 network units. Of course, the a greater or lesser amount of network units may be used, depending on the application. In one example, the LSTM model may comprise an input module, a sequence modelling module and a predictive module. The input module may receive entries from users and/or the system (e.g., 802-806) and map them to entries using previously defined equivalences. These entries are then fed to the embedding layer. The embedding layer receives the entry IDs and transforms them into embeddings with semantic meaning. This layer may be configured as trainable, and able to learn during the training process. The layer weights may be initialized using the values obtained by using the Word2Vec algorithm. The entry embeddings obtained in the input module are then processed by the sequence modelling module.

The LSTM layer of module 810 may be operatively coupled to a predictive module 830, which uses the sequence models created by the LSTMs to generate predictions. This module may be configured using densely connected layers with different types of activations. These densely connected layers may comprise a first fully connected layer 814 and a second fully connected layer 818, with each respectively coupled to a dropout regulation module (816, 820). These connected layers are configured to learn to predict the next user characteristic that may affect the notification schedule on the basis of the models extracted by the previous layers The dropout regulation modules 816, 820 are configured to address overfitting for the fully connected layers 814, 818, since the fully connected layers may occupy most of the parameter. At each training stage, individual nodes are either "dropped out" of the net with probability 1-$p$ or kept with probability p, so that a reduced network is left; incoming and outgoing edges to a dropped-out node may also be removed. In some illustrative embodiments, only the reduced network is trained on the data in that stage. The removed nodes are then reinserted into the network with their original weights. In some illustrative embodiments, the probability that a hidden node will be dropped during the training stages may be 0.5, although other probabilities may be utilized, depending on the application. For input nodes, this may be much lower, because information is directly lost when input nodes are ignored. At testing time, after training has finished, a sample average of all possible $2^n$ dropped-out networks may be determined if a small enough value n is being used. Alternately or in addition, an approximation may be determined by using the full network with each node's output weighted by a factor of p, so the expected value of the output of any node is the same as in the training stages. By avoiding training all nodes on all training data, dropout decreases overfitting, improves training speed, and reduces node interactions, leading them to learn more robust features that better generalize to new data.

Predictive module 830 may be configured with a plurality of blocks of densely connected layers (814, 818) with rectified linear unit (ReLU) activations. ReLU is particularly advantageous for intermediate densely connected layers in both classification and prediction problems. Each of these layers (814, 818) may be configured with a predetermined size (e.g., 1024 network units). After the ReLU activation, a larger dropout regularization may be used (e.g., with a value of 0.8). Finally, a third fully connected layer with a softmax activation function module 822 to obtain the next predictions as output. During operation the most probable characterizations for user entries are used for a given sequence.

Figure 9A:
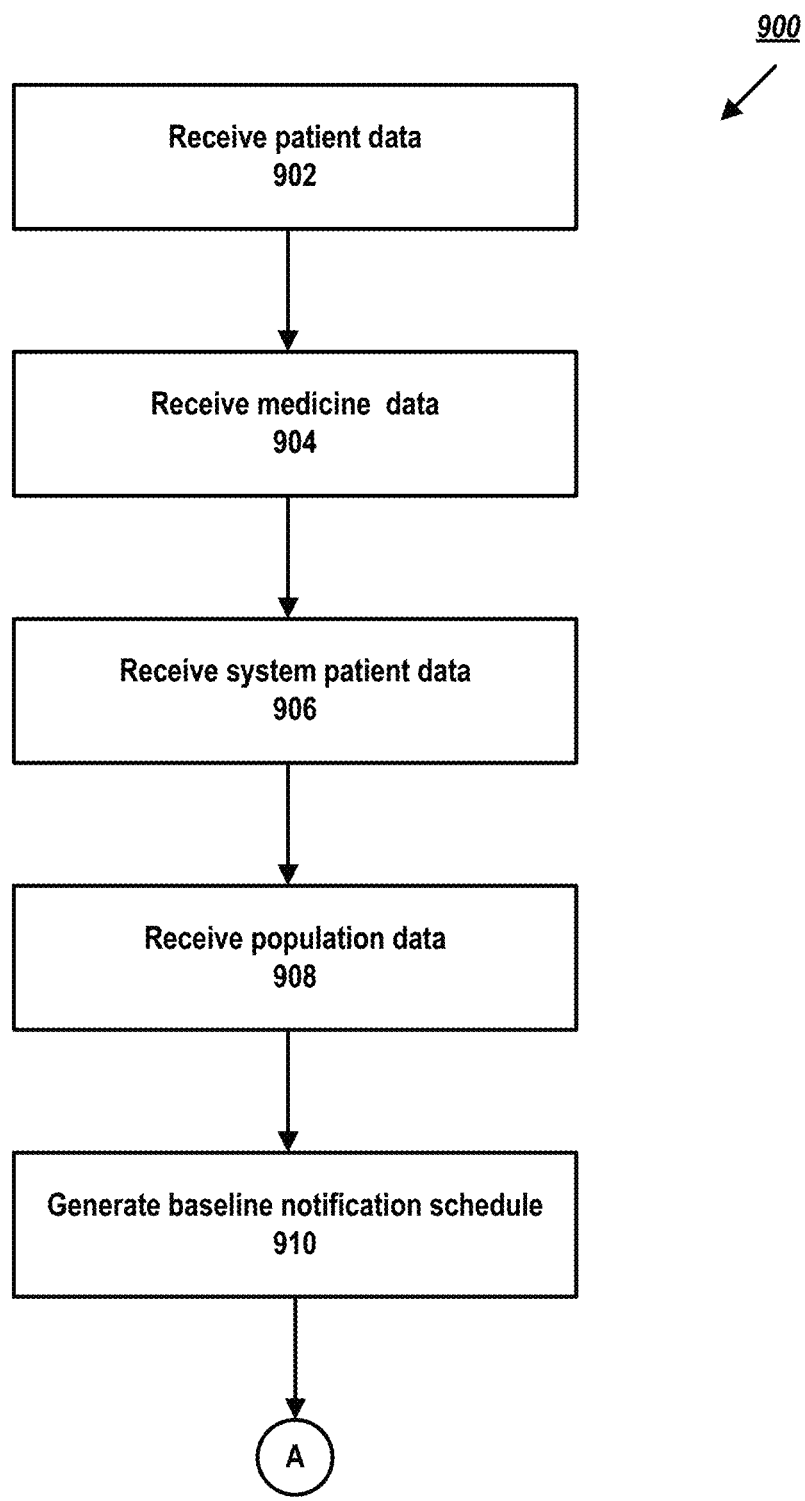
FIG. 9A shows a process for performing statistical and/or predictive processing for generating a baseline notification schedule.

Turning to FIG. 9A, the drawing shows a process 900 for performing statistical and/or predictive processing for generating a baseline notification schedule under an illustrative embodiment. In block 902, the system (e.g., 100) receives patient data associated with a patient participating in a medical regimen. In block 904, the system (e.g., 100) receives medicine data associated with the patient. In block 906, the system (e.g., 100) receives system patient data (e.g., 808) associated with other patients in the system. The patient data in block 906 may additionally include medicine data pertaining to each respective other patient. In block 908, the system (e.g., 100) receives population data, which may be associated with population data module 812 of FIG. 8. From this information, the system will generate a baseline notification schedule in block 910 for transmitting notifications as described above.

Figure 9B:
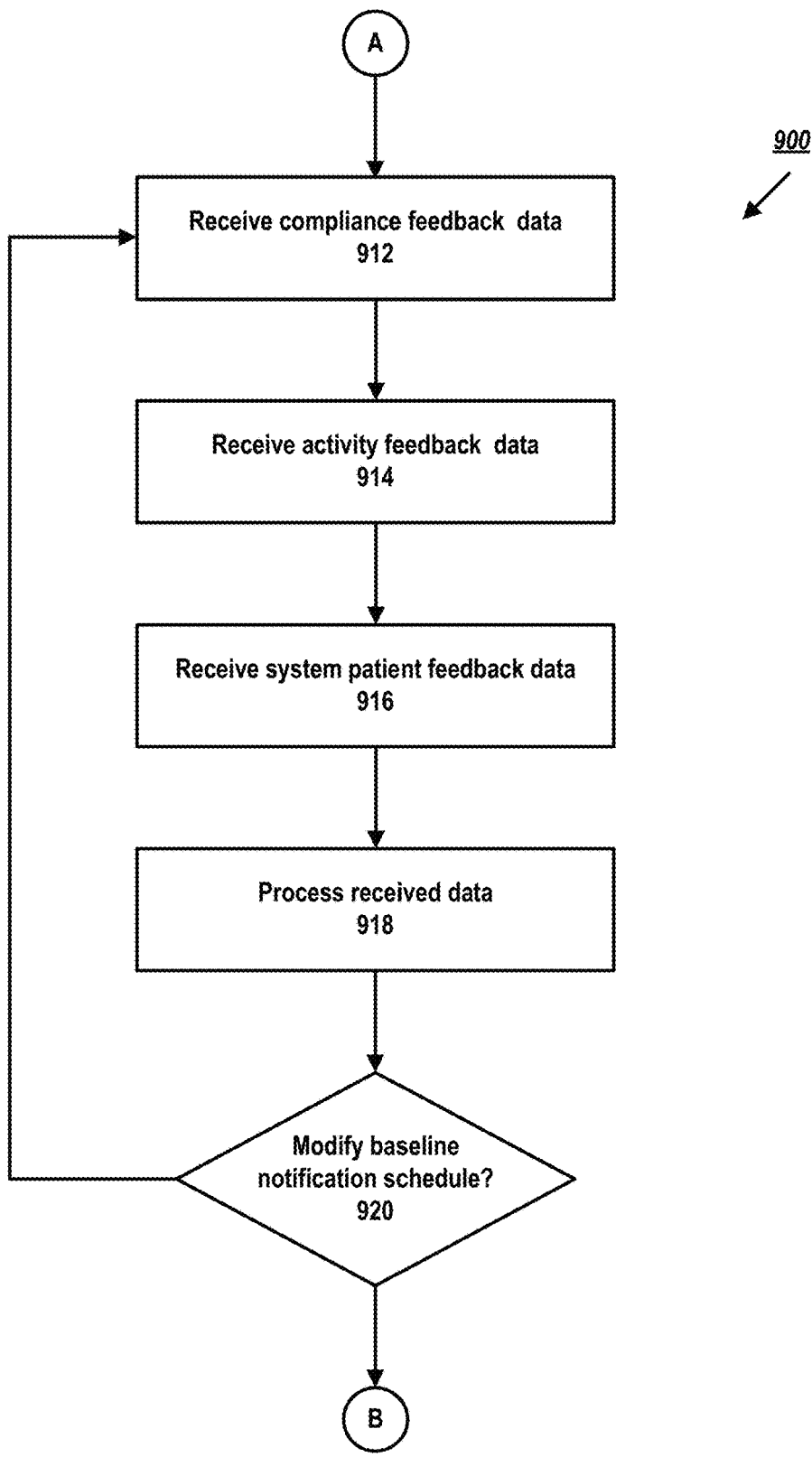
FIG. 9B shows a continuation of the process of FIG. 9A for receiving and processing feedback data for modifying the baseline notification schedule.

FIG. 9B shows a continuation ("A") of the process of FIG. 9A for receiving and processing feedback data for modifying the baseline notification schedule under an illustrative embodiment. Here, the baseline notification schedule represents an initial notification schedule that is configured before receiving feedback during the course of a medication regimen. In some illustrative embodiments, the baseline notification schedule may incorporate feedback and other associated data from previous medication regimens and thus incorporate the "best" statistical/predictive data as known at the start of a new medication regimen. Once the medication regimen is started, the user's device (e.g., 408-412) communicates with the system via a server (e.g., 404) and/or other suitable hardware and software on the user's device allows the user to begin providing feedback data. In block 912, the system (e.g., 100) receives medicine/compliance feedback data (e.g., 802, 806). Additionally, the system may receive activity feedback data (e.g., 804) in block 916 and system patient feedback data (e.g., 808) in block 916. Those skilled in the art will recognize that the order of receiving feedback data is not important to the present disclosure. Additionally, the system may be configured to receive some, but not all of the feedback data discussed above in connection with FIG. 8.

In block 918, the system (e.g., 100) processes the received data (e.g., any or all of 902-908, 912-916) to perform statistical/predictive analysis. In block 918, the system may learn and/or determine a predicted patient characteristic that may warrant modification of the baseline schedule. Turning to decision block 920, if a predicted patient characteristic is not present that warrants baseline schedule modification ("NO"), the process 900 reverts back to block 912, where the process continues to receive further feedback data. If a predicted patient characteristic warranting baseline notification schedule modification is present ("YES"), the process 900 continues to FIG. 9C ("B"). In some illustrative embodiments, a single patient characteristic may warrant modification of the baseline notification schedule. Alternately or in addition, multiple patient characteristics, and/or specific combinations of characteristics nay be determined and/or predicted for modifying the baseline notification schedule.

Figure 9C:
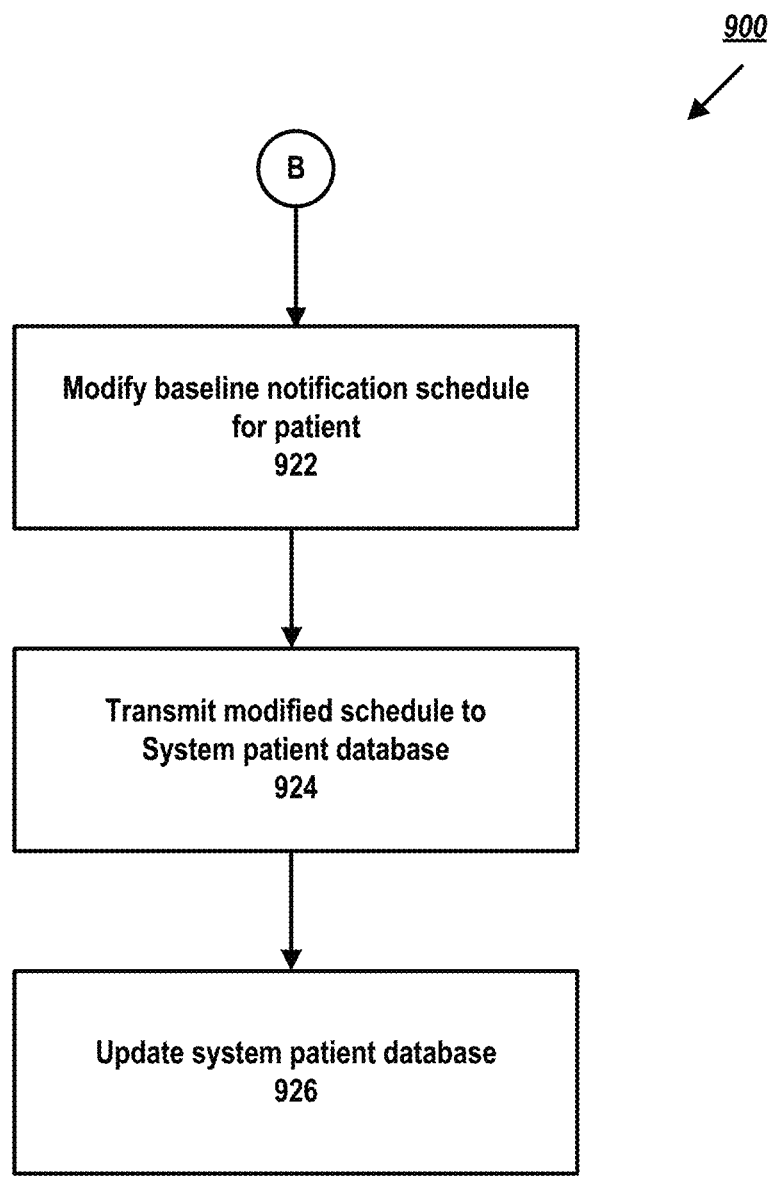
FIG. 9C shows a continuation of the process of FIG. 9B for modifying the baseline notification schedule for a patient and to update a system patient database.

FIG. 9C shows a continuation of the process 900 of FIG. 9B for modifying the baseline notification schedule for a patient and to update a system patient database. In block 922 the baseline notification schedule for the patient is modified. This modification may include, but is not limited to, increasing or decreasing the frequency of notifications, remove, add or modify existing notifications and/or the contents thereof, and transmitting, or causing activation of, additional interfaces (e.g., dialog box, interactive word cloud, etc.) to the patient device for further patient input. Once modified, the system then transmits the modified schedule to the system patient database (e.g., 706) so that the system may update the data for other patient similarly situated as the patient in block 926. Once updated, the system patient database (e.g., 706) may be configured transmit the updated system patient data on subsequent statistical/predictive processing (e.g., via 800).

The technologies and techniques disclosed herein provide a system for processing data to predict patient characteristics in order to modify a notification schedule pursuant to a medicinal regimen. Using an input on their device, patients may submit demographic and/or personal information and medicinal information to create a profile for each patient for a baseline notification schedule. Patients may then provide further inputs via their devices during the medicinal regimen to give feedback on any of a number of aspects of their lives. For example, if a patient goes jogging, eats a particular food, takes a vitamin or supplement, experiences a headache or sleepiness, watches a particular television show, entertains friends, takes a medication early or late, and so on, the system receives and process this data to predict the likelihood the patient will be compliant or not with the following dosage in the medicinal regimen. As the system collects more of this data, the system learns the patient characteristic and subsequently becomes "smarter" with respect to the notification schedule frequency, content, and interactive data that is provided to the user. In turn, the patient is better served by having a notification system that is optimized for their circumstances, while the system administrator is better served by having an efficient notification system that does not needlessly utilize network resources.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A system for configuring resource-efficient notifications in a medical computer system, comprising:
   a portal processor;
   a communications interface, operatively coupled to the portal processor, wherein the communications interface is configured to receive patient data and patient feedback data associated with a patient; and
   a portal database, operatively coupled to the portal processor, wherein the portal database comprises system patient data associated with other patients,
   wherein the portal processor is configured to
      process a data model for medical regimen data to calculate a baseline notification schedule based on the patient data, wherein the baseline notification schedule comprises content and notification frequency for individual notifications,
      automatically process the patient data and/or patient feedback data to determine word vectors and embedded vectors,
      execute statistical/predictive processing on the processed patient data and/or patient feedback data to determine a patient characteristic,
      determine an access matrix for the baseline notification schedule, the access matrix comprising at least one group encryption level and security class for recipients of the baseline notification schedule,
      modify, via the portal processor, the baseline notification schedule based on the determined patient characteristic to form a modified schedule for transmission in the system, wherein one or more messages of the modified schedule for transmission are configured with the at least one group encryption level and security class, and
      transmit the one or more messages of the modified baseline notification to the medical computer system, wherein access to the transmitted one or more messages is restricted according to the at least one group encryption level and security class.

2. The system of claim 1, wherein the portal processor is configured to execute statistical/predictive processing using a neural network model.

3. The system of claim 2, wherein the neural network model comprises a long short-term memory (LSTM) model.

4. The system of claim 2, wherein patient feedback data comprises a representation of words comprising at least one of identifications, strings, and/or one-hot vectors, and wherein the portal processor is configured to execute natural language processing (NLP) with the representation of words.

5. The system of claim 4, wherein the NLP comprises embeddings to represent the words in a semantic context.

6. The system of claim 1, wherein the communications interface is configured to receive system patent data from at least one other patient, and wherein the portal processor is configured to perform statistical/predictive processing on the system patient data together with the patient feedback data to determine the patient characteristic.

7. The system of claim 6, wherein the communications interface is configured to receive population data, and wherein the portal processor is configured to perform statistical/predictive processing on the population data together with the system patient data and the patient feedback data to determine the patient characteristic.

8. A processor-based method for configuring resource-efficient notifications in a medical computer system, comprising:
   receiving, via a communications interface, patient data and patient feedback data associated with a patient;
   storing, via a portal database, system patient data associated with other patients,
   processing a data model for medical regimen data, via a portal processor, to calculate a baseline notification schedule based on the patient data, wherein the baseline notification schedule comprises content and notification frequency for individual notifications,
   automatically processing, via the portal processor, the patient data and/or patient feedback data to determine word vectors and embedded vectors from the patient data,
   executing, via the portal processor, statistical/predictive processing on the processed patient feedback data to determine a patient characteristic,
   determining an access matrix for the baseline notification schedule, the access matrix comprising at least one group encryption level and security class for recipients of the baseline notification schedule, and
   modifying, via the portal processor, the baseline notification schedule based on the determined patient characteristic to form a modified schedule for transmission in the system, wherein one or more messages of the modified schedule for transmission are configured with the at least one group encryption level and security class; and
   transmitting the one or more messages of the modified baseline notification to the medical computer system, wherein access to the transmitted one or more messages is restricted according to the at least one group encryption level and security class.

9. The processor-based method of claim 8, wherein executing statistical/predictive processing comprises executing a neural network model.

10. The processor-based method of claim 9, wherein the neural network model comprises a long short-term memory (LSTM) model.

11. The processor-based method of claim 8, wherein patient feedback data comprises a representation of words comprising at least one of identifications, strings, and/or one-hot vectors, and wherein the portal processor is configured to execute natural language processing (NLP) with the representation of words.

12. The processor-based method of claim 11, wherein the NLP comprises embeddings to represent the words in a semantic context.

13. The processor-based method of claim 8, wherein the communications interface is configured to receive system patent data from at least one other patient, and wherein the portal processor is configured to perform statistical/predictive processing on the system patient data together with the patient feedback data to determine the patient characteristic.

14. The processor-based method of claim 13, wherein the communications interface is configured to receive population data, and wherein the portal processor is configured to perform statistical/predictive processing on the population data together with the system patient data and the patient feedback data to determine the patient characteristic.

15. A system for configuring resource-efficient notifications in a medical computer system, comprising:
   a portal processor;
   a communications interface, operatively coupled to the portal processor, wherein the communications interface is configured to receive patient data and patient feedback data associated with a patient; and
   a portal database, operatively coupled to the portal processor, wherein the portal database comprises system patient data associated with other patients,
   wherein the portal processor is configured to
      process a data model for medical regimen data to calculate a baseline notification schedule based on the patient data, wherein the baseline notification schedule comprises content and notification frequency for individual notifications,
      automatically process the patient data and/or patient feedback data to determine word vectors and embedded vectors from the patient data,
      execute statistical/predictive processing using a neural network model on the processed patient feedback data to determine a patient characteristic,
      determine an access matrix for the baseline notification schedule, the access matrix comprising at least one group encryption level and security class for recipients of the baseline notification schedule,
      modify, via the portal processor, the baseline notification schedule based on the determined patient characteristic to form a modified schedule for transmission in the system, wherein one or more messages of the modified schedule for transmission are configured with the at least one group encryption level and security class, and
      transmit the one or more messages of the modified baseline notification to the medical computer system, wherein access to the transmitted one or more messages is restricted according to the at least one group encryption level and security class.

16. The system of claim 15, wherein the neural network model comprises a long short-term memory (LSTM) model.

17. The system of claim 15, wherein patient feedback data comprises a representation of words comprising at least one of identifications, strings, and/or one-hot vectors, and wherein the portal processor is configured to execute natural language processing (NLP) with the representation of words.

18. The system of claim 17, wherein the NLP comprises embeddings to represent the words in a semantic context.

19. The system of claim 15, wherein the communications interface is configured to receive system patent data from at least one other patient, and wherein the portal processor is configured to perform statistical/predictive processing on the system patient data together with the patient feedback data to determine the patient characteristic.

20. The system of claim 19, wherein the communications interface is configured to receive population data, and wherein the portal processor is configured to perform statistical/predictive processing on the population data together with the system patient data and the patient feedback data to determine the patient characteristic.

* * * * *